US00PP26970P3

(12) United States Plant Patent
Lintott et al.

(10) Patent No.: US PP26,970 P3
(45) Date of Patent: Jul. 19, 2016

(54) ***GAILLARDIA* PLANT NAMED 'SUNSET CUTIE'**

(50) Latin Name: *Gaillardia×grandiflora*
Varietal Denomination: Sunset Cutie

(71) Applicants: Keith George Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 79 days.

(21) Appl. No.: 14/544,057

(22) Filed: Nov. 19, 2014

(65) Prior Publication Data

US 2015/0150178 P1 May 28, 2015

Related U.S. Application Data

(60) Provisional application No. 61/963,168, filed on Nov. 25, 2013.

(51) Int. Cl.
*A01H 5/00* (2006.01)

(52) U.S. Cl.
USPC ..... Plt./431

(58) Field of Classification Search
USPC ..... Plt./431
See application file for complete search history.

*Primary Examiner* — Annette Para
(74) *Attorney, Agent, or Firm* — Bethany R. Roahrig; Barbara Campbell; Cochran Freund & Young, LLC

(57) ABSTRACT

A new cultivar of *Gaillardia* named 'Sunset Cutie' that is distinguishable by a long blooming period, a compact, low-growing habit and large inflorescences composed of two rows of flat ray florets which are ruby in color, with a yellow border, is disclosed.

2 Drawing Sheets

Genus and species: *Gaillardia×grandiflora* .
Variety denomination: 'Sunset Cutie'.

BACKGROUND

The present disclosure relates to a new and distinct cultivar of *Gaillardia* plant, also known as a blanket flower, a herbaceous perennial that is grown for use as an ornamental landscape and container plant. The new variety is known botanically as *Gaillardia×grandiflora* and will be referred to hereinafter by the variety name 'Sunset Cutie'. *Gaillardia* is in the family Compositae, under which the commonly referred to "flower" is actually the inflorescence, and made up of smaller ray florets and disc florets. The ray florets themselves have the appearance of "petals".

'Sunset Cutie' originated and was selected from a large population of hybrid seedlings from a *Gaillardia* breeding program started in 2006. The breeding program was conducted in a greenhouse nursery in West Sussex, United Kingdom. The aims of the breeding program were to produce novel combinations of flower colors and flower forms which are borne on well-branched plants with sturdy growth habits. The inventors carried out a controlled hybridization using combinations of selected named varieties and selected unnamed and unreleased seedlings retained from previous breeding cycles. 'Sunset Cutie' was selected in 2010 for its large flowers comprised of two rows (layers) of ruby colored ray florets whose tips are yellow. 'Sunset Cutie' flowers continually from spring until fall. 'Sunset Cutie' was also selected for its compact and naturally branching habit.

The hybridization which led to the selection of 'Sunset Cutie' was carried out during 2009 using a proprietary unreleased seedling known as 'G801-3' (unpatented) as the male parent and a proprietary unreleased seedling known as 'G5' (unpatented) as the female parent. 'Sunset Cutie' was selected by the inventors in 2010.

'Sunset Cutie' was first asexually propagated in September 2010 in a greenhouse at the inventors nursery in West Sussex, United Kingdom using shoot cuttings taken from lateral branches. 'Sunset Cutie' is stable and reproduces true to type in successive generations of asexual reproduction.

SUMMARY

The following traits have been repeatedly observed and represent the distinguishing characteristics of 'Sunset Cutie'. 'Sunset Cutie' has not been tested under all possible conditions and phenotypic differences may be observed with variations in environmental, climatic, and cultural conditions, without however, any variance in genotype.

1. 'Sunset Cutie' exhibits a compact and naturally branching plant habit.
2. 'Sunset Cutie' exhibits single inflorescences composed of two rows of flat ray florets which are ruby in color, with a yellow border.
3. The disc of 'Sunset Cutie' is deep red in color, with a yellow center, when the inflorescence is fully expanded.
4. 'Sunset Cutie' blooms continually from early spring until late fall.
5. 'Sunset Cutie' is very floriferous over a long blooming period.
6. After one year's growth in a 3 liter container, 'Sunset Cutie' is 35 cm to 40 cm in height and 40 cm to 45 cm in width.
7. 'Sunset Cutie' is hardy in USDA zone 5.

DESCRIPTION OF THE PHOTOGRAPHS

The accompanying color photographs illustrate the overall appearance of the new *Gaillardia* cultivar 'Sunset Cutie' showing the colors as true as it is reasonably possible to obtain in colored reproductions of this type. Colors in the photographs may differ from the color values cited in the detailed botanical description, which more accurately describes the actual colors of the new variety 'Sunset Cutie'.

DESCRIPTION OF THE NEW VARIETY

Figure 1:
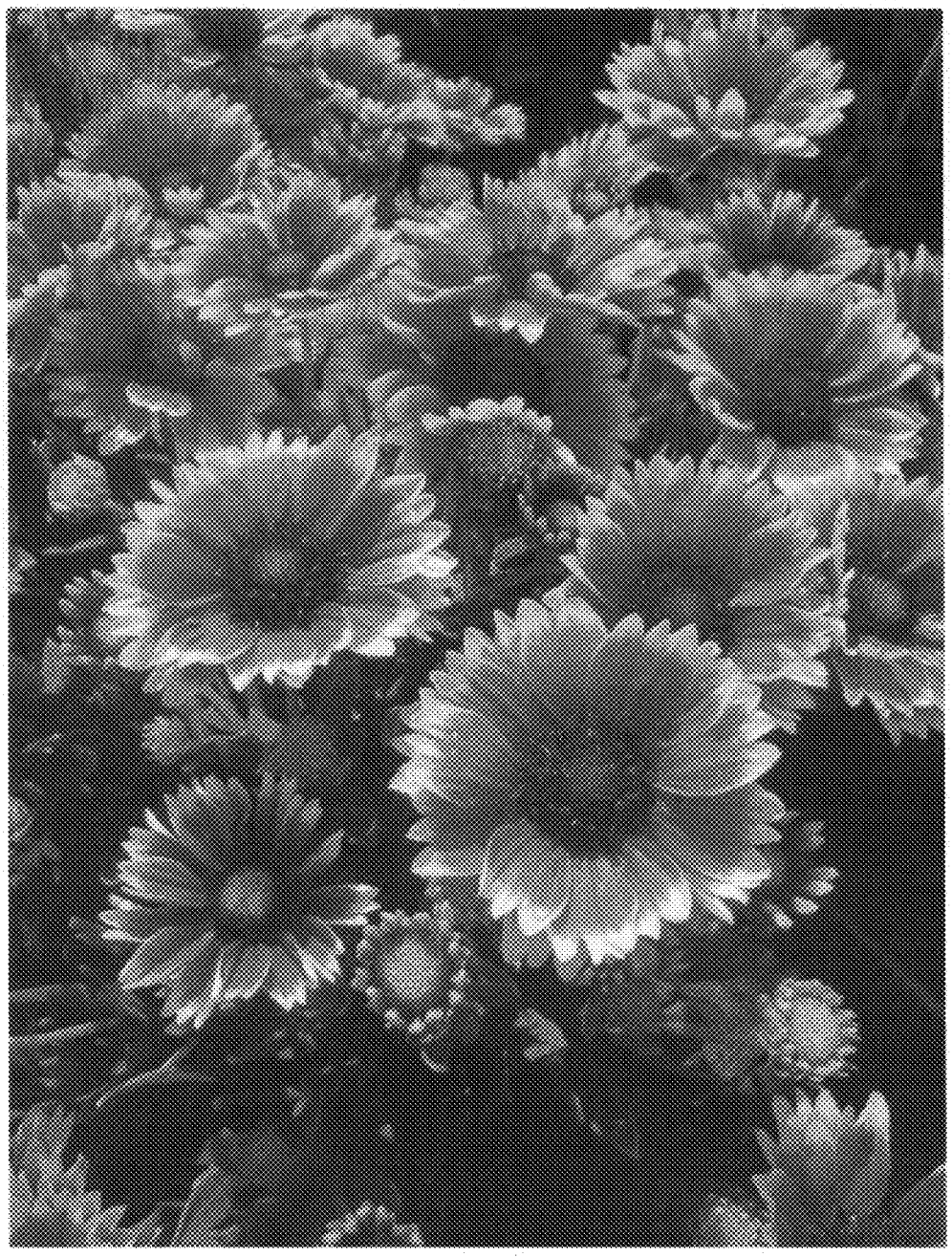
FIG. 1 depicts a whole plant of 'Sunset Cutie' which has been grown in a frost-free greenhouse in West Sussex, United Kingdom. The illustrated plant is one year old and has been grown without any pinching or chemical growth regulator.
Figure 2:
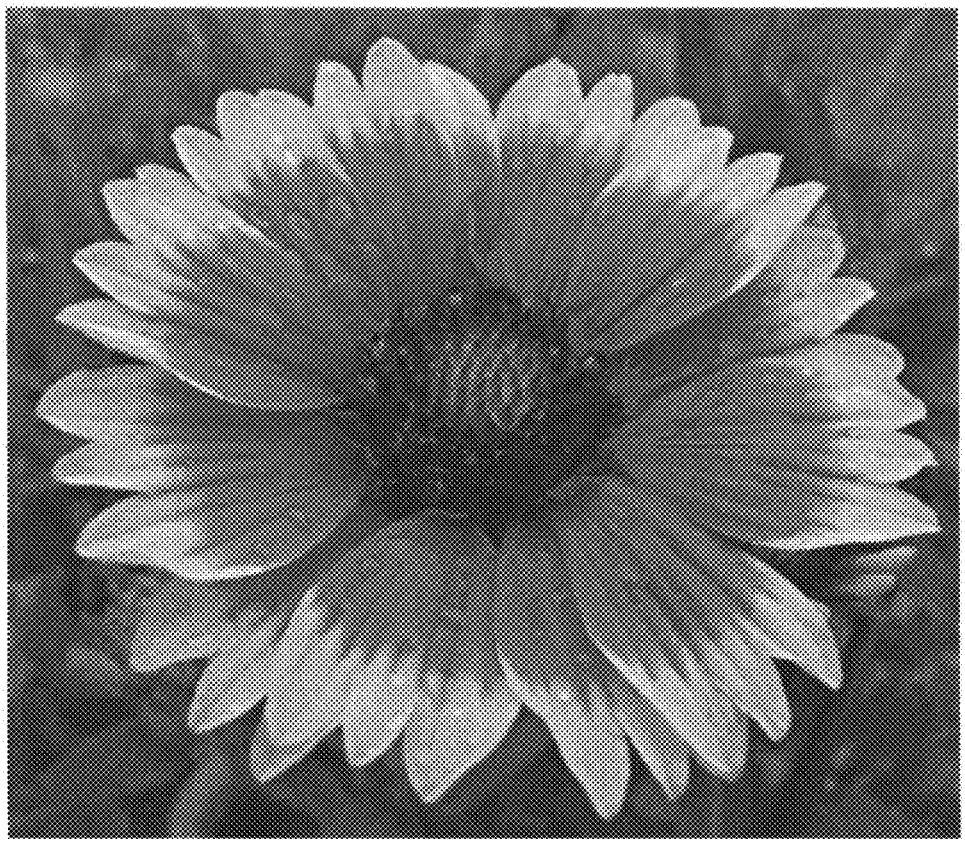
FIG. 2 depicts a close-up view of the fully expanded inflorescence of 'Sunset Cutie'.

The following detailed descriptions set forth the distinctive characteristics of 'Sunset Cutie'. Observations, measurements, values, and comparisons were collected in August, 2014 in Santa Barbara, Calif. from a one year old plant grown outdoors in full sun in freely drained proprietary peat-based potting soil. Color determinations were made in accordance with The 2007 Royal Horticultural Society Colour Chart from London England, except where general color terms of ordinary dictionary significance are used.

Classification:

*Family*.—Compositae.

*Genus*.—*Gaillardia*.

*Species*.—×*grandiflora*.

*Common name*.—Blanket flower.

Parentage:

*Female parent*.—*Gaillardia* code number 'G5' (unpatented).

*Male parent*.—*Gaillardia* code number 'G801-3' (unpatented).

Plant:

*Propagation method*.—Typically by softwood cuttings although root cuttings have also been successful.

*Root system*.—Fine and fibrous.

*Vigor*.—Moderate vigor.

*Time to initiate roots*.—Approximately 14 to 20 days are needed to develop roots on initial cuttings.

*Temperatures to initiate rooting*.—The recommended air temperature is 20-21° Centigrade.

*Crop time*.—Approximately 10 weeks to 2 months are needed to produce a finished 15 cm container plant from a rooted cutting.

*Growth habit*.—Compact and naturally freely branching.

*Suggested container size*.—15 cm container.

*Use*.—Ornamental for use as a landscape plant or container plant.

*Type*.—Herbaceous perennial.

*Plant dimensions*.—After one year's growth in a 3 liter container: 35 cm to 40 cm in height and 40 cm to 45 cm in width; at maturity in the ground: 40 cm to 45 cm in height and 50 cm to 55 cm in width.

*Cultural requirements*.—Grow in full sun with moderate water, and well-draining soil such as loam.

*Hardiness*.—USDA Zone 5.

*Growing requirements*.—If grown outside in regions which experience winter freezing, 'Sunset Cutie' may be started as a cutting during the spring or summer of the previous year, planted out prior to the onset of winter, and flowering will commence typically in May or June according to the region and season. When grown outside in frost-free regions, or in frost-protected greenhouses, 'Sunset Cutie' will flower virtually all year round and may be started as a cutting (which should be non-flowering) at any time of year.

Stems:

*Branching habit*.—Basal branching.

*Stem color*.—138B.

*Stem dimensions*.—10 cm to 15 cm in length and 4 mm to 5 mm in width.

*Stem shape*.—Cylindrical, slightly fluted longitudinally.

*Stem surface*.—Markedly villous with dense coverage of very fine silvery hairs, approximately 3 mm to 4 mm in length.

*Internode length*.—Average internode length is 10 mm to 12 mm.

Foliage:

*Type*.—Evergreen.

*Leaf arrangement*.—Alternate.

*Margin*.—Entire.

*Leaf shape*.—Oblanceolate, except occasional basal leaf bears one or two pairs of opposite lobes.

*Leaf dimensions* (*lobes absent*).—7.5 cm in length, 1.5 cm in width.

*Leaf dimensions* (*lobes present*).—7.5 cm in length, 1.7 cm in width at lobes.

*Leaf base*.—Truncate.

*Leaf apex*.—Acute.

*Leaf attachment*.—Sessile.

*Leaf color* (*both surfaces*).—138C.

*Leaf venation pattern*.—Parallel. Mid vein protrudes on both surfaces.

*Vein color* (*both surfaces*).—138B.

*Leaf surface* (*both surfaces*).—Pubescent, very fine silvery hairs, lighter than 156D, approximately 3 mm in length.

*Fragrance*.—A slight sage-like scent when bruised.

Inflorescence:

*Inflorescence*.—Solitary.

*Aspect*.—Facing upward.

*Dimensions of inflorescence*.—70 mm in diameter and 15 mm in height.

*Inflorescence type*.—Radiate capitate with central disc.

*Disc diameter* (*inflorescence fully expanded*).—20 mm to 22 mm.

*Inflorescence number per plant*.—A one-year old plant bears approximately 25 to 30 inflorescences in bud and flower at one time.

*Blooming season*.—Spring, summer and fall.

*Lastingness of inflorescence on the plant*.—7 days, reducing to 4 days in full sun in mid-summer.

Peduncle:

*Peduncle dimensions*.—7 cm to 9 cm in length and 2.0 mm in diameter.

*Peduncle shape*.—Cylindrical.

*Peduncle surface*.—Surface is pubescent and exhibits longitudinal ridges.

*Peduncle color*.—138B.

*Peduncle strength*.—Stiff.

Flower buds:

*Bud shape*.—Rotate whorl.

*Bud dimensions* (*bud*).—10 mm in diameter and 6 mm in length.

*Bud color*.—138B.

*Bud surface*.—Villous.

Ray florets:

*Ray floret shape*.—Fan shaped with 2 or 3 fused petals appearing as lobes.

*Ray floret surface texture*.—Adaxial surface: Pubescent. Abaxial surface: Glabrous.

*Ray floret arrangement*.—Radiate.

*Number of ray floret per inflorescence*.—18 to 20.

*Number of petals per ray floret*.—Three.

*Fused or unfused*.—Petals are basally fused.

*Petal margins of ray florets*.—Entire.

*Ray floret dimensions*.—3.0 cm in length including the corolla tube, 14 mm in width at the widest point.

*Corolla tube dimensions*.—5 mm in depth and 0.5 mm in diameter.

*Ray floret color* (*upper surface*).—42A, except lobes 13A.

*Ray floret color* (*lower surface*).—53D, except lobes 13A.

*Ray floret veins* (*both surfaces*).—Longitudinal, parallel, fine but prominent, visible in petal blade as darker red 46A, not visible in yellow lobes.

*Self-cleaning or persistent*.—Self-cleaning.

Disc florets:

*Quantity of disc florets per inflorescence*.—Numerous, approximately 200 to 250.

*Disc floret dimensions* (*including pistil length*).—9 mm in length and 2.5 mm in width.

*Depth of disc floret corolla tube*.—6 mm.

*Surface of disc florets*.—Lanate.

*Color of disc florets* (*inflorescence newly opening, both surfaces*).—12A.

*Color of disc florets* (*inflorescence fully expanded, both surfaces*).—N34A.

*Phyllary*.—Dimensions: 5.50 cm in diameter and 3 cm in length. Color: 147B. Arrangement: Whorl.

*Involucral bracts*.—Number: An average of 25 per inflorescence. Shape: Oblanceolate. Dimensions: 2 cm in length and 0.50 cm in width. Margin: Entire. Apex: Acute. Base: Truncate. Color (both surfaces): 138B. Surface texture (both surfaces): Pubescent.

*Fragrance of inflorescence*.—Sweet fragrance.

Reproductive organs:

*Stamens* (*present on disc florets only*).—Number: Three, adnate to inner surface of corolla tube. Dimensions: 0.2 mm in width and 5 mm in length. Color: 17A. Form: Plumose. Anther: Dimensions: 0.50 mm in length and 1 mm in width. Color: 187A. Shape: Narrow lanceolate. Pollen: Present. Quantity: Large amount. Color: 17C.

*Pistil* (*present on ray florets and disc florets*).—Number: One per floret. Length: 12 mm. Style dimensions: 2 mm in length and 1 mm in width. Style color: 150D. Stigma: Dimensions: 8 mm in length and 1.75 mm in width. Form: Plumose. Color: 187A. Shape: Bifurcate. Ovary: Position: Inferior. Color: 150D. Shape: Globose. Dimensions: 1 mm in width and 2 mm in height.

Fruit/seed set:

*Number of seeds*.—Small to moderate amount (ranges from 50-100 seeds per inflorescence.

*Seed dimensions*.—5 mm to 6 mm in length (including hairs at apex) and 1-2 mm in diameter.

*Seed color*.—200A.

*Seed shape*.—Conical with rounded base and apex.

*Seed surface*.—Smooth except at apex where many very fine silver hairs, up to 2 mm in length, are present in circular groups.

Disease and pest susceptibility: 'Sunset Cutie' has not been observed to exhibit any resistance to any particular pest or disease. 'Sunset Cutie' is susceptible to downy mildew and to thrips as may be typical of *Gaillardia*.

COMPARISON WITH PARENTAL LINES AND KNOWN VARIETY

'Sunset Cutie' is distinguishable from the female parent, 'G5' as follows: Whereas the female parent exhibits dark red-purple flowers, the flowers of 'Sunset Cutie' are predominantly ruby in color, with a yellow border. 'Sunset Cutie' also exhibits a more compact growth habit than the female parent. Finally, 'Sunset Cutie' has noticeably darker foliage than the female parent.

'Sunset Cutie' is distinguishable from the male parent, 'G801-3' as follows. Whereas the male parent exhibits tubular shaped flowers, the flowers of 'Sunset Cutie' consist of two (layers) of flat ray florets. 'Sunset Cutie' has a longer flowering period than the male parent.

The variety of *Gaillardia* which is considered to most closely resemble 'Sunset Cutie' is the variety, 'Goblin' (unpatented). The flowers of 'Goblin' are red-bronze with yellow tips whereas the flowers of 'Sunset Cutie' are ruby in color, with a yellow border. Additionally, 'Sunset Cutie' flowers over a longer period of time and produces more flowers than 'Goblin'.

We claim:

1. A new and distinct cultivar of *Gaillardia* plant named 'Sunset Cutie' as described and illustrated herein.

* * * * *